(12) United States Patent
Giordana et al.

(10) Patent No.: US 6,610,333 B1
(45) Date of Patent: Aug. 26, 2003

(54) FEED SUPPLEMENT FOR ARTHROPODS

(75) Inventors: Barbara Giordana, Milan (IT); Maria Giovanna Leonardi, Milan (IT); Paolo Parenti, Cantu (IT)

(73) Assignee: Universita Degli Studi di Milano, Milano (IT)

( * ) Notice: Subject to any disclaimer, the term of this patent is extended or adjusted under 35 U.S.C. 154(b) by 0 days.

(21) Appl. No.: 09/720,454

(22) PCT Filed: Jun. 21, 1999

(86) PCT No.: PCT/EP99/04282

§ 371 (c)(1),
(2), (4) Date: Feb. 26, 2001

(87) PCT Pub. No.: WO00/00041

PCT Pub. Date: Jan. 6, 2000

(30) Foreign Application Priority Data

Jun. 26, 1998 (IT) .......................... MI98A1469

(51) Int. Cl.⁷ ............................ A23K 1/16; A23K 1/18; A01K 67/04
(52) U.S. Cl. ........................................ 426/2; 426/656
(58) Field of Search ..................... 426/2, 656

(56) References Cited

U.S. PATENT DOCUMENTS

| | | | |
|---|---|---|---|
| 3,328,170 A | | 6/1967 | Hamamura et al. ............... 99/2 |
| 3,952,115 A | * | 4/1976 | Damico et al. ............. 426/590 |
| 4,000,318 A | * | 12/1976 | Ferguson et al. ............. 426/2 |
| 4,172,148 A | * | 10/1979 | Hauck et al. ............... 424/311 |

FOREIGN PATENT DOCUMENTS

| | | |
|---|---|---|
| EP | 0 004 334 | 10/1979 |
| JP | 45-5427 | 2/1970 |
| JP | 52-117786 | 10/1977 |
| JP | 54-111480 | 8/1979 |
| JP | 58-203902 | 11/1983 |

OTHER PUBLICATIONS by George C. Rock et al., "Utilization of Methionine Analogues by *Argyrotaenia velutinana* Larvae", *Annals of the Entomological Society of America*, vol. 66, No. 1, pp. 177–179, 1973.

* cited by examiner

*Primary Examiner*—Chhaya D. Sayala
(74) *Attorney, Agent, or Firm*—Young & Thompson

(57) ABSTRACT

A feed supplement for arthropods, in particular for lepidopteran larvae, comprising a low alkyl ester of a biologically active acid or alpha-amino acid. Said alkyl esters of a biologically active acid or alpha-amino acid have general formula (I), in which: X is hydrogen or $NH_2$; $R_1$ is a straight or branched alkyl or alkenyl group, containing 3 to 6 carbon atoms, optionally substituted with at least one hydroxy, carboxylic, amino, amido, guanidyl, thio, methylthio, phenyl or imidazolyl group; and $R_2$ is a group selected from methyl, ethyl and propyl.

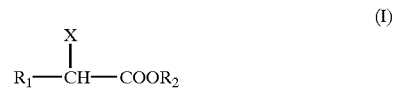

(I)

9 Claims, 1 Drawing Sheet

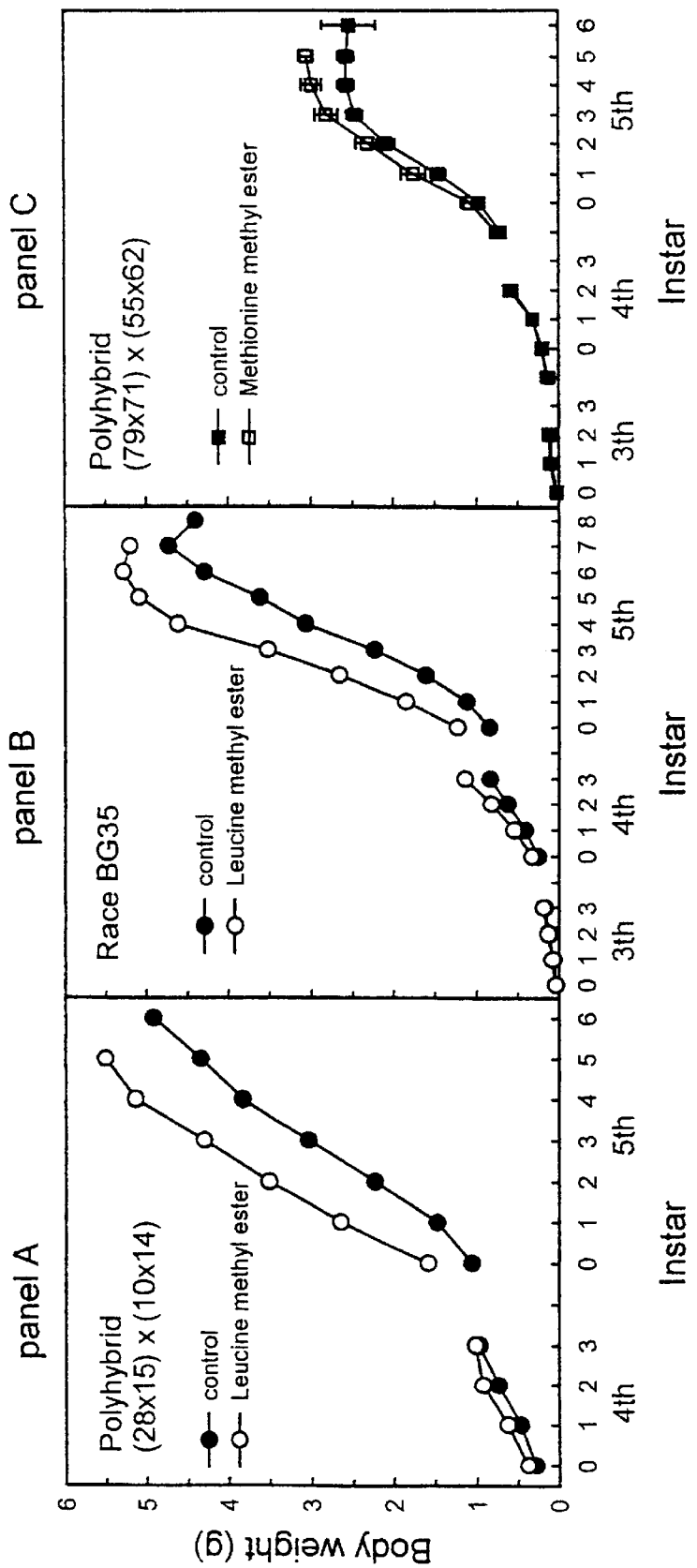
FIGURE

FEED SUPPLEMENT FOR ARTHROPODS

The present invention relates to a feed supplement for arthropods, in particular for lepidopteran larvae and more particularly for larvae of the common silkworm species known as *Bombyx mori*.

More precisely, the present invention relates to a feed supplement capable of inducing the absorption of nutritional molecules from feed by intestinal cells of the lepidopteran larvae, in particular silkworms, as well as a faster growth of the larvae and a remarkable reduction of mortality.

G. C. Rock et al., in "Utilization of methionine analogues by *Argyrotaenia velutinana* larvae" Ann. Entomol. Soc. Am, Vol 66 (no 1) 1973:177–179 discloses that L-methionine ethyl ester may substitute methionine as a sulphur source in the diet of the arthropode *A. velutinana*.

*Bombyx mori* silkworm is known to be used for the production of silk yarn.

The production of silk yarn and its transformation are very important from the economical and commercial point of views, and remarkable efforts have been made to improve production while decreasing costs and making the growth of these larvae faster.

*Bombyx mori* silkworm larva is strictly monophagous in that it only feeds on, mulberry leaves (*Morus alba* or *nigra*). This behavior is a serious drawback and limitation in sericulture, in that mulberry leaves are not available all the year round, they are exposed to atmospheric pollution and to parasites and, when treated with pesticides, they can transmit said substances to the animal.

Furthermore, growing, harvesting and administering mulberry leaves remarkably affect rearing costs.

In order to obviate these drawbacks, artificial diets have been studied and proposed, containing essential nutrients for larval growth in low but still sufficient amounts so as to cause no alterations of the alimentary behavior and of the growth of the larvae, and a certain percentage of mulberry leaf powder for inducing the larvae to accept such feed. Among the essential nutrients, of particular relevance is the protein source. It is, in fact, known that amino acids are the primary source of energy for weight growth of silkworms and for silk biosynthesis and that the subsequent development and fertility depend on the type of the protein source.

Moreover, a number of polyphagous polyhybrids have been selected, capable of accepting artificial diets containing low-cost nutrients, particularly as regards the protein source.

The main drawback of such selection is that the selected hybrids very often produce silk of lower quality than that produced by larvae reared on mulberry leaves. Moreover, for all types of silkworms, the larval life cycle, particularly the fifth instar, during which the feed uptake by the larvae is the highest, is very long and, in many cases, mortality in the first three larval instars is considerable.

Therefore, an object of the present invention is to induce a faster growth of the larvae, increasing the body weight and decreasing the duration of larval instars, in particular of the fifth instar, thereby reducing the whole rearing cycle.

A further object of the present invention is to reduce mortality, particularly in the first three larval instars and to produce last instar larvae and pupae of higher weight than with a normal feeding cycle.

More precisely, the object of the present invention is to provide activating molecules capable of enhancing the assimilation of the ingested protein substances, administered together with natural diet or introduced as a component of artificial diets.

The inventors found that lower alkyl esters of biologically active acids or alpha-amino acids are capable of promoting the absorption of nutritional molecules from diet by the intestinal cells of the larvae, inducing a faster growth and a significant reduction of mortality of the larvae.

According to a first aspect, the present invention provides a feed supplement comprising a low alkyl ester of a biologically active acid or alpha-amino acid and the use thereof for the preparation of both natural and artificial diets for arthropods.

According to a further aspect, the present invention relates to a feed composition comprising a natural or artificial feed for arthropods and a low alkyl ester of a biologically active acid or alpha-amino acid.

According to a further aspect, the present invention relates to a method for inducing a fast growth of lepidopteran larvae, in particular *Bombyx mori*, increasing their body weight and decreasing the duration of larval instars, thereby reducing the whole rearing cycle, as well as decreasing mortality, which method consists in administering orally said animals with a feed supplement consisting of a low alkyl ester of a biologically active acid or alpha-amino acid.

According to the invention, preferred arthropods are lepidopteran larvae, more particularly larvae of the common silkworm *Bombyx mori*.

Low alkyl esters of biologically active acids or of alpha-amino acids are compounds well known in literature. These compounds can be represented by the following general formula:

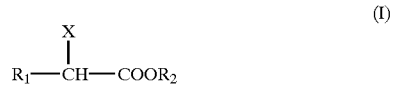

(I)

in which:

X is hydrogen or $NH_2$;

$R_1$ is a straight or branched alkyl or alkenyl group, containing 3 to 6 carbon atoms, optionally substituted with at least one hydroxy, carboxylic, amino, amido, guanidyl, thio, methylthio, phenyl or imidazolyl group; and $R_2$ is a group selected from methyl, ethyl and propyl.

Particularly active for the purposes of the present invention are compounds of formula (I) in which X is $NH_2$ and $R_1$ is an alkyl group containing 4 carbon atoms, more preferably those in which X is $NH_2$ and $R_1$ is a branched alkyl group containing 4 carbon atoms.

Examples of compounds of general formula (I) useful as feed supplements according to the present invention are methyl, ethyl and propyl esters of the following acids and alpha-amino acids: 4-methyl-valeric acid, 4-methyl-3-pentenoic acid, 3-methyl-valeric acid, 3-methyl-3-pentenoic acid, L-alanine, L-valine, L-leucine, L-isoleucine, L-methionine, L-threonine, L-aspargine, L-arginine, L-glutamine, L-lysine, L-phenylalanine and L-histidine.

Most preferred compounds are L-leucine and L-methionine methyl and ethyl esters.

The alkyl esters of acids or alpha-amino acids of the present invention can be added to natural or artificial diet, preferably as aqueous solutions. Solutions having concentrations ranging from 0.1 to 2 mM can be used.

The solution is added to the artificial diet or it can be sprayed on the natural diet.

The amount of alkyl ester of a biologically active acid or alpha-amino acid to be added to the diet can range within wide limits, depending on the type of diet and on the species of arthropods. Amounts ranging from 10 to 500 mg/kg of natural or artificial diet can be used.

In vivo tests carried out by the inventors on both polyhybrids and races of Bombyx mori have proved that the addition of an alkyl ester of a biologically active acid or alpha-amino acid to natural and artificial commercial diet gives the following results:

faster growing of the larvae, with an increase in body weight and a decrease in the duration of larval instars, with consequent reduction of at least 24 hours on the whole rearing cycle;

remarkable reduction of mortality in the first three larval instars;

formation of last instar larvae and pupae of higher weight than the control;

production of cocoon shells of weight significantly higher than control, particularly in larvae selected for rearing on artificial diets.

In no cases case alterations of metamorphosis or lower fertility of the adults were evidenced.

DESCRIPTION OF THE FIGURE

Increase in body weight during the fourth and fifth instar for the polyhybrid (28×15)×(10×14) B. mori (panel A) and during the last three instars for the race BG35 (panel B) in silkworms reared on artificial diet (control) and on diet added with leucine methyl ester. Panel C reports the increase in body weight during the last three instars for the polyhybrid (79×71)×(55×62) reared on artificial diet added with methionine methyl ester.

The following examples further illustrates the present invention without limiting it.

EXAMPLE 1

The effect of different esters and aminoesters was tested in vitro by measuring the uptake of radiolabeled leucine into membrane vesicles purified from the midgut tissue of B. mori larvae.

Uptakes were measured by incubating 10 μl of membrane vesicles and 40 μl of a isosmotic mixture buffered at pH 10.8 and containing 0.1 mM L-leucine, 30 μCi/ml of L-[3H]-leucine as a tracer and 0.2 mM of the substances indicated. Incubations were stopped after 7 seconds by 75-fold dilution in an ice-cold isotonic saline and filtration through cellulose filters (0.2 μm mesh). Filters were then counted for radioactivity in a scintillation counter and data were expressed per mg of membrane proteins. Vesicles were prepared by calcium precipitation and differential centrifugation from Bombyx mori larval midgut according to standard biochemical protocols.

As shown in the following Table 1, all the tested molecules were able to increase amino acid uptake into the vesicles. Leucine methyl ester and moethyonine methyl ester were then chosen for the in vivo experimentation.

TABLE 1

| Condition | Leucine uptake (pmol/7s/mg membrane protein) |
|---|---|
| None | 450 ± 20 |
| Leucine methyl ester | 4500 ± 150 |
| Norleucine methyl ester | 3800 ± 100 |
| Methionine methyl ester | 4000 ± 180 |
| 4-methylvaleric methyl ester | 2600 ± 80 |
| 3-methylvaleric methyl ester | 800 ± 30 |
| Leucine ethyl ester | 2200 ± 75 |

EXAMPLE 2

Artificial diet for Bombyx mori, commercialized by KYO-YA Co. Ltd Kyoto, Japan, was added with 130 mg of L-leucine methyl ester (Figure, panels A and B) or 200 mg of L-methionine methyl ester (Figure, panel C) per 1 kg of diet.

The resulting supplemented diet was administered to 20 members of the Bombyx mori polyhybrid (28×15)×(10×14) and race BG 35 for L-leucine methyl ester and the polyhybrid (79×71)×(55×62) for L-methionine methyl ester, all provided by I.S.Z.A, Section Specialized for Sericulture, Padua, Italy. The same numbers of larvae of the two polyhybrid and of the race were reared on the same non-supplemented diet for comparison (control).

The Figure reports the growths of larvae of both polyhybrid and race, determined as increase in body weight at various larval instars.

As it can be observed, the increase in body weight, expressed as g/larva, is clearly evident already at the fourth instar and is significantly different at the fifth instar, compared with the untreated larvae.

The following Table 2 reports mortality percentages in the first three larval instars.

TABLE 2

| | Percent of mortality | |
|---|---|---|
| | Control | Leucine methyl ester |
| Polyhybrid (28 × 15) × (10 × 14) | 19 | 0 |
| Race 21 Molucelli | 30 | 20 |

The obtained data, compared with the control, clearly show the significant reduction of mortality in the larvae treated according to the present invention.

Finally, Table 3 reports the weight of cocoon shells from larvae fed with the supplement of the present invention and the control.

TABLE 3

| | Weight of cocoon shell (g) | |
|---|---|---|
| | Control | Leucine methyl ester |
| Polyhybrid (28 × 15) × (10 × 14) | 0.32 ± 0.02 | 0.46 ± 0.03 |
| Race BG35 | 0.25 ± 0.02 | 0.31 ± 0.01 |

The increase in weight of cocoon shells obtained with the feed supplement of the invention is about 20% by weight.

What is claimed is:

1. A method for increasing the growth or reducing the mortality of arthropods, or for reducing the duration of larval instars or of an entire rearing cycle of arthropods, which comprises orally administering to said arthropods a methionine-containing diet including a feed supplement which comprises an alkyl ester of general formula (I):

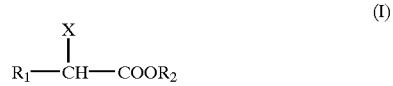

(I)

in which

X is hydrogen or $NH_2$;

$R_1$ is a straight or branched alkyl or alkenyl group, containing 3 to 6 carbon atoms, optionally substituted with at least one hydroxy, carboxylic, amino, amido, guanidyl, thio, methylthio, phenyl or imidazolyl group; and $R_2$ is a group selected from methyl, ethyl and propyl.

2. The method according to claim 1, in which the alkyl esters of formula (I) in which X is $NH_2$ and $R_1$ is an alkyl group containing 4 carbon atoms.

3. The method according to claim 2, in which X is $NH_2$ and $R_1$ is a branched alkyl group containing 4 carbon atoms.

4. The method according to claim 1, in which the alkyl ester is selected form methyl, ethyl and propyl esters of the following acids and alpha-amino acids: 4-methylvaleric acid, 4-methyl-3-pentenoic acid, 3-methylvaleric acid, 3-methyl-3-pentenoic acid, L-alanine, L-valine, L-leucine, L-isoleucine, L-methionine, L-threonine, L-aspargine, L-arginine, L-glutamine, L-lysine, L-phenylalanine and L-histidine.

5. The method according to claim 4, in which the alkyl ester is L-leucine or L-methionine methyl or ethyl ester.

6. The method according to claim 1, in which the feed supplement has a content of alkyl ester of a biologically active acid or alpha-amino acid from 10 to 500 mg per kg of natural or artificial feed.

7. The method according to claim 1, in which the feed supplement is administered as a 0.1–2 mM aqueous solution.

8. The method according to claim 1, in which the arthropods are lepidopteran larvae of silkworm *Bombyx mori*.

9. The method according to claim 1, in which the arthropods are lepidopteran larvae.

* * * * *